United States Patent [19]

Burnette et al.

[11] Patent Number: 4,866,999
[45] Date of Patent: Sep. 19, 1989

[54] CORROSION CRACKING TEST SPECIMEN AND ASSEMBLY

[75] Inventors: Colin Burnette; Juri Kolts, both of Ponca City, Okla.

[73] Assignee: Conoco Inc., Ponca City, Okla.

[21] Appl. No.: 234,345

[22] Filed: Aug. 18, 1988

[51] Int. Cl.[4] .............................................. G01N 3/20
[52] U.S. Cl. .......................................... 73/87; 73/853; 428/596; 436/6
[58] Field of Search ................... 73/87, 849, 853, 854, 73/788, 799; 436/6; 267/158, 164, 165; 428/596, 597

[56] References Cited

U.S. PATENT DOCUMENTS

| | | |
|---|---|---|
| 481,207 | 8/1892 | Smith ............................ 428/596 X |
| 2,831,342 | 4/1958 | Adler et al. ........................... 73/826 |
| 3,068,688 | 12/1962 | Gunnert ................................ 73/783 |
| 3,192,766 | 7/1965 | Keys ..................................... 73/834 |
| 3,196,670 | 7/1965 | Lander .................................. 73/834 |
| 3,277,693 | 10/1966 | D'Amato et al. ....................... 73/12 |
| 3,455,152 | 7/1969 | Maker ..................................... 73/87 |
| 3,479,866 | 11/1969 | Movich et al. ......................... 73/86 |
| 3,680,367 | 8/1972 | Krafft ................................... 73/799 |
| 3,761,385 | 9/1973 | Ruthel et al. ................... 428/596 X |
| 4,461,168 | 7/1984 | Kobayashi .............................. 73/87 |

Primary Examiner—Jerry W. Myracle
Attorney, Agent, or Firm—Richard W. Collins

[57] ABSTRACT

A corrosion cracking test assembly comprising a pair of strips each having notches formed along one edge and assembled in a stressed condition.

3 Claims, 2 Drawing Sheets

CORROSION CRACKING TEST SPECIMEN AND ASSEMBLY

BACKGROUND OF THE INVENTION

This invention relates to hydrogen embrittlement and stress corrosion cracking of metals, and particularly of corrosion resistant alloys. Hydrogen embrittlement (HE) and stress corrosion cracking (SCC) are important phenomena that impact many industrial operations. Laboratory test results are being used increasingly to assess the performance of steels and especially corrosion-resistant alloys toward hydrogen embrittlement and stress corrosion cracking. Because of the wide differences in responses of various corrosion-resistant alloys to corrosive environments, galvanic effects become especially important in assessing HE and SCC resistance. Also, most present methods of stressing samples involve the use of specimen restraining fixtures. To test a number of alloys and to avoid galvanic effects, a large number of fixtures are required. The costs and time to obtain these fixtures are high. Therefore, a need existed for a method of stressing samples without the associated problem of galvanic corrosion or the need to use fixtures to stress the samples.

Recent reports show that about one-third of present deep well completions in the U.S. use corrosion-resistant alloys for corrosion control. Many of these deep wells will be acidized using either hydrochloric acid or mixtures that include HCl. Therefore, the likelihood of HCl contacting various corrosion-resistant alloys is quite high. Most of the experimental work on effects of acidizing environments on corrosion-resistant alloys has emphasized general corrosion, especially at elevated temperatures. However, some evidence shows that stress corrosion cracking can result with the presence of $H_2S$ in room temperature hydrochloric acid. Since the dissolution of sulfide-containing scales during acidizing may provide a source of sulfide ions, this form of cracking must be considered in using corrosion-resistant alloys. Corrosion inhibition can mitigate stress corrosion cracking in HCl; however only cursory examinations have been made of inhibition on cracking behavior of corrosion resistant alloys.

Because of the many requirements for stress corrosion cracking tests in HCl, a new test sample assembly was needed. Testing fixtures sufficiently resistant to corrosion in $HCl+H_2S$ to provide freedom from solution contamination and sufficient strength were not readily available. In addition, the time and cost needed to manufacture testing fixtures from exotic alloys is excessive. Therefore, a system was needed to stress the samples without the requirement for stressing fixtures. While there are stressing methods available that do not require fixtures, these methods are either not quantitative with respect to applied stress (i.e., u-bends), or require welding.

One type of prior art test assembly is a "double cantilever" assembly comprising a metal bar having a slot formed in one end. A wedge is driven into the slot to provide stress, and the assembly with the wedge is then subjected to the test environment. These assemblies also include grooves extending along their length and holes formed to attach to devices for application of tensile forces. The amount of machining required for these assemblies is excessive in situations where large numbers of tests are to be run, such as when a particular alloy is to be tested over a wide range of temperatures or with a range of corrosive fluids.

SUMMARY OF THE INVENTION

According to the present invention, a test sample assembly is provided that permits stressing of alloys without the need for expensive fixtures. The configuration involves the machining of only two slots into blank strips of the alloy to be tested. Multiple samples can be machined simultaneously. The resulting stresses correlate adequately with calculated values, at least for low stress levels.

It is accordingly an object of the present invention to provide test sample assemblies that are simple, inexpensive, and easily produced in various sizes. This objective is accomplished as will be apparent from the following detailed description of the preferred embodiment.

THE DRAWINGS

DESCRIPTION OF THE PREFERRED EMBODIMENT

Figure 1:
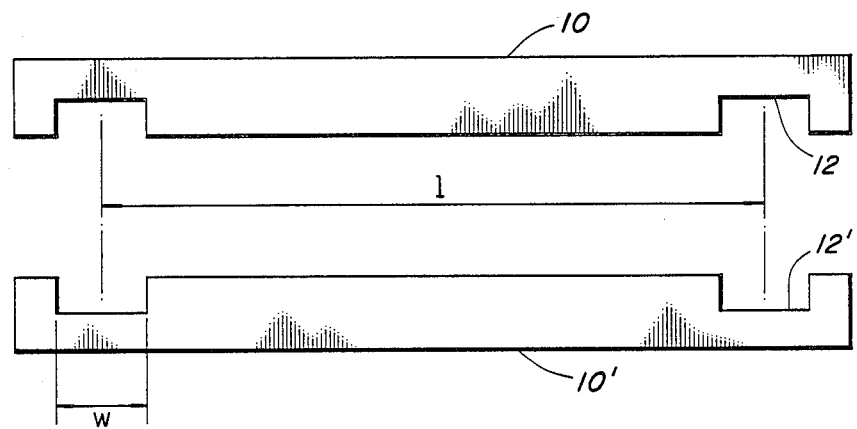
FIG. 1 is a plan view of a pair of test specimens in accordance with the invention.
Figure 2:
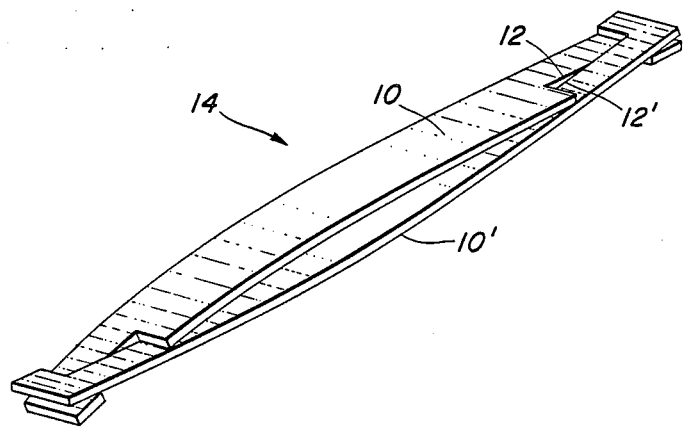
FIG. 2 is a perspective view of a pair of test specimens forming a test assembly in accordance with the invention.

The preferred embodiment of the test specimen and the test assembly in accordance with the invention is illustrated in FIGS. 1 and 2.

THE TEST SPECIMEN

As shown in FIG. 1, a pair of substantially identical flat strips of metal 10 and 10' each having a length, width and thickness are provided with rectangular notches 12 and 12' respectively having a notch width w formed proximate each end of the respective strip and on the same lengthwise edge of the respective strip. The notches are formed through the thickness of the strips and extend into the strips for one half the width of the strips. The sides of notches 12 and 12' are perpendicular to the lengthwise edge of strips 10 and 10' respectively, and the inner edges of notches 12 and 12' are parallel to the lengthwise edge of strips 10 and 10' respectively.

THE TEST ASSEMBLY

Referring to FIG. 2, a pair of test specimens are assembled to provide a test assembly 14. The assembly is formed by setting a notch 12 of specimen 10 over a notch 12' in specimen 10', and then bending one or both specimens until the other notches in the specimens are matched and assembled with each specimen bowed outwardly with respect to the other. Since the notches have a depth of one half the width of the specimens, the assembly has a width equal to the width of the individual specimens. This simplifies the calculations as will be apparent from the description of the strain calculation technique. The strain on the test assembly is determined by the width and separation of the notches and the thickness of the specimens.

CALCULATION OF SPECIMEN STRAIN

Figure 3:
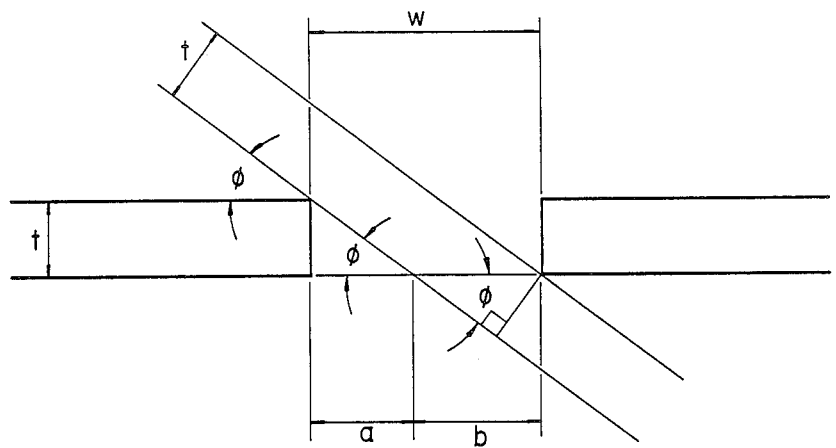
FIGS. 3 and 4 are schematic illustrations of test assemblies used in calculating strain on samples.

The strain on the assembly obtained by combining two individual specimens can be calculated from simple geometry if it is assumed that the radius of curvature remains constant throughout the stressed portion of the specimen. FIG. 3 displays the specimen configuration at the points of contact at each end of the specimens. In effect, the strain obtained is from four line contacts (two lines at each end).

The width of the notch (w) from FIG. 3 is:

$$w = a + b = \frac{t}{\tan \phi} + \frac{t}{\sin \phi} \quad (1)$$

Figure 4:
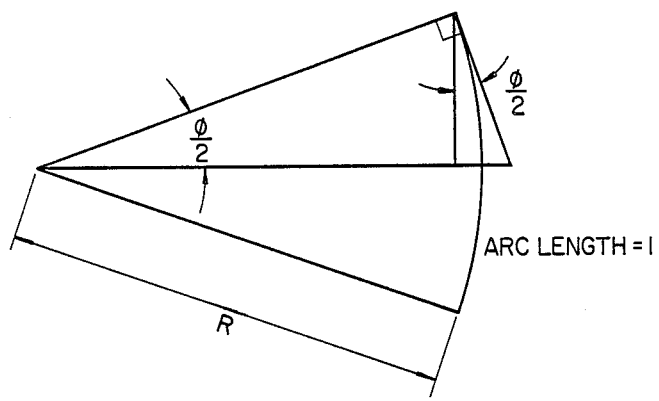

FIG. 4 represents the specimen configuration when stressed (arc of a circle). The strain on the outer fiber is given by:

$$\epsilon = \frac{t}{2R} \quad (2)$$

The equation for the length of an arc of a circle is:

$$l = \frac{\pi R \phi}{180} \quad (3)$$

combining Equations 2 and 3, the angle in degrees is:

$$\phi = \frac{360 \epsilon l}{\pi t} \quad (4)$$

where:
w = width of notch
l = length of specimen between midpoints of notches
t = specimen thickness
$\phi$ = angle between samples at notches
$\epsilon$ = outer fiber strain Thus using Equations 4 and 1, the notch dimensions for a desired strain can be calculated.

Notice that stress is not a parameter in any of the above equations. To obtain a given stress, the strain corresponding to a given stress should be read from a stress-strain curve, and the samples should then be machined to obtain the corresponding strain. This is an advantage for austenitic alloys since the stress-strain curves are not linear near the yield point of the alloys.

VERIFICATION OF SPECIMEN STRAINS

Measurements were made using standard strain gage techniques to compare calculated and actual strains on a stressed sample. Table 1 reports the mechanical properties of the nickel base austenitic alloy used in evaluating the sample. Traditionally, the yield stress is defined by the intersection of the 0.2% offset line with the stress-strain curve. The strains at the yield point may vary around 4-8% for duplicate specimens. This variation should increase for lower yield strength materials due to the shape of the stress-strain curve at lower strength levels. An alternative definition for the yield stress in low strength steels is the stress at a strain of 0.005.

Table II shows the correlation between measured and calculated values of strain for three strain levels. The measured values are somewhat lower than the calculated values.

The deviation from calculated values increases with increasing strain. This can be caused by deformation at the slot locations and by the nonlinear stress-strain behavior at the yield point of the alloy. At the yield point, these deviations become quite large. While the deviations of strain between calculated and measured values may seem quite high, the differences between calculated and measured stresses are smaller due to the shape of the stress-strain curves. For example, a 30% difference is calculated versus measured strains found for the alloy at the yield point actually produces a difference of 10% in stress level between calculated and measured values. Considering the variability in mechanical behavior between specimens, the errors produced in stressing the samples are acceptable. These errors are of the order found in techniques presently used where linear-elastic stress equations are employed for stress calculations in austenitic alloys.

TABLE I
MECHANICAL PROPERTIES OF ALLOY

| Alloy | Thickness Inches | Yield Strength Ksi | Tensile Strength Ksi |
|---|---|---|---|
| Nickel Base | .067 | 181 | 195 |
|  |  | 177 | 187 |

TABLE II
COMPARISON OF CALCULATED AND MEASURED STRAINS OF SAMPLES
Nickel Base Alloy
0.067-Inch Thick Samples
l = 4 Inches
t = .067 Inches

| Slot Width w (Inches) | Calculated Strain | Measured Strain Average of 5 Measurements |
|---|---|---|
| .639 | .00175 | .00164 |
|  |  | .00148 |
| .404 | .00275 | .00229 |
| .238 | .0046 | .00294 |
|  |  | .00320 |

USE OF THE TEST ASSEMBLIES

The use of test assemblies 14 involves immersing one or more (usually several) assemblies in a particular corrosive liquid, such as hydrochloric acid saturated with hydrogen sulfide, for a period of time. If the test is performed in glassware, it is sometimes desirable to insert the assembly 14 into a hollow inert tube to protect the glass in the event of sample assembly breakage under stress. High temperature tests are generally conducted in autoclaves, and hollow inert tubes can be used to prevent metal-to-metal contact of the assemblies.

At the end of the test, the assemblies are removed, and if not broken, are examined for evidence of cracking.

MANUFACTURE OF TEST SPECIMENS

Test specimens can be manufactured in large numbers at low cost by assembling a number of blank sample strips and simultaneously forming notches of a predetermined width and distance apart.

This invention enables a large number of tests to be run for the cost of a single run using prior art techniques requiring specimen-holding fixtures or double cantilevered wedge assemblies. Further, the desired strain for a particular test can be obtained by selecting strips of appropriate length and thickness combined with appropriate size and spacing of notches formed therein.

We claim:

1. A metal test specimen comprising a flat metal strip having a length, width and thickness, said strip having a first smooth lengthwise edge and said strip having a rectangular notch formed in the other lengthwise edge thereof proximate each end thereof, said other lengthwise edge being smooth except for said notch proximate each end thereof, each of said notches extending through the thickness of said specimen to a depth which is one half the width of said specimen.

2. A self-stressed metal test assembly comprising a pair of substantially identical metal test specimens, each of said specimens comprising a flat metal strip having a length, width and thickness and having a rectangular notch formed therein proximate each end thereof, each of said notches extending through the thickness of said specimen and to a depth which is one half the width of said specimen, each of said notches being formed on a common edge along the length of said specimen, the notches of each of said specimens being spaced apart the same distance along the length of the respective specimens, and the pair of specimens being in a stressed condition by virtue of the notches of each specimen being interlocked with the notches of the other specimen such that the width of the assembly is the same as the width of each individual specimen, each of said specimens being bowed outwardly with respect to the other.

3. A self-stressed metal test assembly in accordance with claim 2 wherein the test specimens are formed of nickel base alloy.

* * * * *